United States Patent [19]

Robar et al.

[11] 4,010,715
[45] Mar. 8, 1977

[54] FLUID CONDUCTIVITY DETECTING MEANS

[75] Inventors: James D. J. Robar; David G. Glass, both of Saskatoon, Canada

[73] Assignee: Seds Systems Ltd., Canada

[22] Filed: June 5, 1975

[21] Appl. No.: 584,069

[30] Foreign Application Priority Data

Oct. 18, 1974 Canada ............................ 211755

[52] U.S. Cl. ............................................. 119/14.14
[51] Int. Cl.² ............................................. A01J 7/00
[58] Field of Search ......... 119/14.14, 14.15, 14.08; 324/30

[56] References Cited

UNITED STATES PATENTS

| | | | |
|---|---|---|---|
| 2,898,549 | 8/1959 | Miller | 119/14.15 X |
| 3,474,330 | 10/1969 | Dauphinee | 324/30 |
| 3,664,306 | 5/1972 | Quayle et al. | 119/14.14 |
| 3,878,819 | 4/1975 | Harman | 119/14.14 |

*Primary Examiner*—Hugh R. Chamblee
*Attorney, Agent, or Firm*—Craig & Antonelli

[57] ABSTRACT

An element used in determining the conductivity of fluids. An insulating tube is provided for carrying the fluid to be measured. Cylindrical electrodes surround the tube at laterally spaced positions. When a signal is applied to the electrodes, the tube and fluid act as dielectric in a capacitor. Measurement of the amount of current passed by the capacitor provides an indication of the conductivity of the fluid. Means is provided to minimize the effect of stray currents.

15 Claims, 7 Drawing Figures

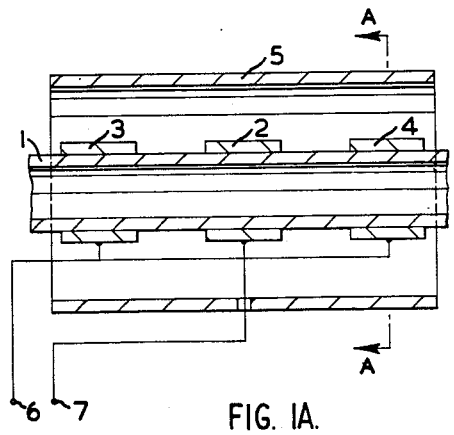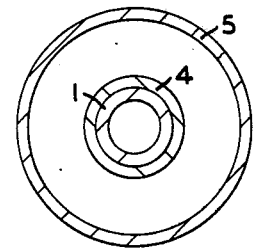
FIG. 1A.  FIG. 1B.
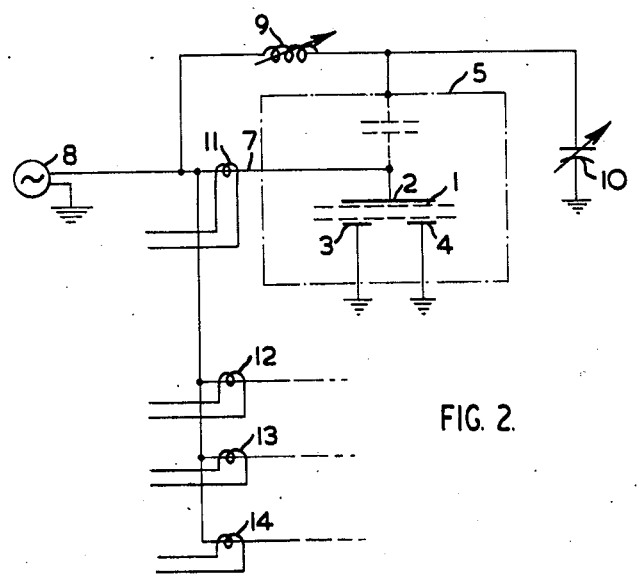
FIG. 2.
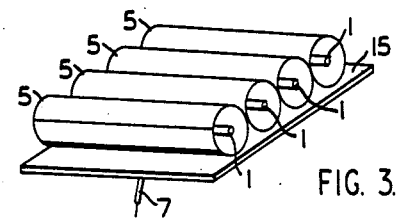
FIG. 3.

FLUID CONDUCTIVITY DETECTING MEANS

This invention relates to a structure for determining the conductivity of a fluid, and particularly to means for passing a current therethrough.

It is known that the electrical conductivity of fluids can be obtained by inducing a current therein, and detecting the amount of induced current, the impedance of the fluid passing more or less current as the case may be. The electrical conductivity must often be known of fluids such as electrolyte solutions, sludges, biological fluids, etc. The conductivity is often indicative of the degree of purity, or of the presence of certain kinds of impurities.

It has been found that the electrical conductivity of milk is affected by such factors as diet, breed of mammal, temperature and phase of lactation cycle. However, within a particular bovine animal, the electrical conductivity ratio between quarters have been found to be relatively constant, within a given amount of error. Conductivity which varies markedly upward in a particular quarter has been found to be indicative of the presence of mastitis, probably due to translocation of salts from the blood to the milk.

It is therefore desirable to provide means for determining the electrical conductivity of milk as it is drawn from each quarter of a cow, prior to mixing, and prior to substantial cooling of the milk from body temperature.

It has been found that the implantation of current inducing electrodes directly into the milk has many disadvantages, including contamination, polarization of the milk, etc. Other methods have been tried, for instance immersion of a pair of toroidal coils, etc. Therefore it has become clear that an electrodeless technique for inducing the current would be highly desirable, since a tube for passing the milk would be unobstructed, and could be fabricated of the most desirable material for passing the milk, to enforce cleanliness, disposability, etc.

An electrodeless technique for inducing current in fluids such as milk is described in U.S. Pat. No. 3,396,331. Here the fluid passage tube contains a loop, the tube entering one side of the loop and leaving the other. Toroids surround opposite sides of the loop. An oscillator connected to one of the toroids induces current into the fluid through the walls of the tube which is picked up in one or more of the other toroids. The amount of current detected is interpolated and provides an indication of the conductivity of the fluid.

In U.S. Pat. No. Re. 24,420, a similar loop in the fluid carrying tube passes through the cores of a pair of transformers. Windings on one core induce the current, and windings on another, in the other part of the loop, pick up the resulting current, and provide an indication of the conductivity.

However, it is clear that mass production of the aforenoted structures for use, for instance, by farmers in routine milking chores to obtain a real-time conductivity measurement is expensive. The winding of toroids around the loop of a fluid-carrying insulating tube has not been found to be economical for mass production. In addition, stray leakage currents have been found to be difficult to eliminate or minimize.

We have found that an electrodeless structure can be fabricated in a conductivity determining apparatus, which does not require the use of toroids wound about a loop in a fluid-carrying tube. The structure may be fabricated easily, uses a minimum of materials, and is thus inexpensive, and therefore suited to mass production application techniques.

Instead of inductively coupling an electrical signal to a fluid, we have found that we are able to capacitively couple the signal thereto. The fluid acts as a dielectric in a capacitor. The amount of alternating current flowing in this capacitor we have found to be a reliable indicator of conductivity of the fluid. In the preferred embodiment of this invention, the amount of current measured will be mainly affected by the fluid-carrying tube inside diameter and the electrode diameter (as well as the conductivity), and thus the current range can be easily established. In addition, leakage currents have been found to be easily minimized.

The apparatus which we have invented for determining the conductivity of fluid, comprises an insulating tube for passing of fluid therethrough, a pair of spaced conducting plates, each separated by a dielectric from the fluid, for capacitively coupling an alternating current signal to the fluid, and means connected to the conductive plates for passing the signal detection means. Preferably, the electrodes are comprised of a first conducting cylinder surrounding and adjacent the dielectric tube, and a pair of conducting cylinders surrounding and adjacent the tube on different sides of the first cylinder, at equally laterally spaced positions, electrically connected together. In addition, a cylindrical shield of diameter greater than the three aforenoted cylinders is preferably coaxially positioned over, but insulated from the electrode cylinders, the length of the shield extending at least approximately 25% of the length of the first cylinder on each side thereof.

While above is described briefly the preferred structure, of course, other forms of electrodes could be fabricated and still meet the intention of the present invention. For instance, the electrodes need not be cylindrical, but may be plates of other shape spaced from the fluid by a dielectric, and usefully can conform to whatever shape the fluid carrying dielectric tube may be in, such as flat sided — V-shaped, oval, etc. Other dielectrics than that used in the tube can also be interposed between the tube and electrodes.

It will be clear that the present invention is useful in the determination of the electrical conductivity of a wide variety of fluids, and, it is by no means intended that it be limited to use for the detection of the conductivity only of milk. However, the description below will be directed to a milk conductivity measuring device, as an example.

A better understanding of the invention will be obtained by reference to the description below, as well as the following figures, in which:

FIG. 1A is a cross sectional elevation view of the preferred embodiment of the fluid conductivity measuring device element;

FIG. 1B is an axial cross sectional view of FIG. 1A, at Section A—A;

FIG. 2 is a schematic circuit used in minimizing the effect of stray capacitance in the invention;

FIG. 3 is a perspective view of a multi-element form of the invention;

Figure 6:
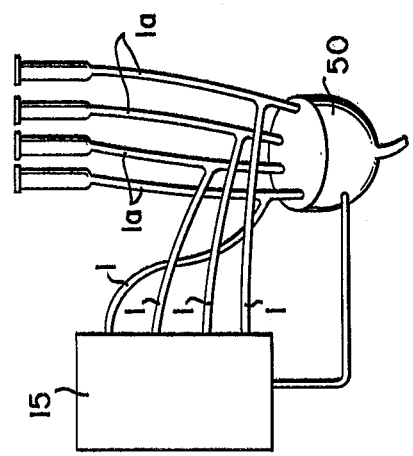
FIG. 6 is a schematic view of a milking apparatus incorporating the present invention.

Turning now to FIGS. 1A and 1B, the preferred embodiment of the conductivity sensor is shown in elevation and axial cross section. A dielectric tube 1 is provided, through which milk is passed during milking. As seen in FIG. 6, the tube usefully is inserted as a bypass to each of the milk tubes 1a which carry the full stream of milk into the mixing bowl 50 normally found in the "claw" of a milking machine. The dielectric tube could be glass, plastic, Nylon, Teflon, rubber, etc. The material is chosen so as to be non-contaminating and non-conducting.

In some structures, the tube 1 may form a section of the main fluid carrying tube 1a. It is important when measuring milk for mastitis that the tube be located as close to the quarter of the cow being measured as possible.

Surrounding and adjacent the dielectric tube is an electrically conducting cylinder 2, which forms one electrode.

A pair of electrically conducting cylinders similar to cylinder 2 are disposed surrounding and adjacent the tube 1 on opposite sides of cylinder 2, at equal axially spaced lateral positions. The pair of cylinders 3 and 4, connected together, form second electrodes of a capacitor. The tube and the milk passing therethrough form the dielectric of the capacitor.

It is preferred that the inside diameter of the tube, for use with milk, be as thin as possible consistent with a reasonable flow rate, and a ⅛ inch diameter has been found to be very suitable. A ½ inch electrode length, with a separation distance between electrodes of ½ inch has been found suitable for use as electrodes. The electrodes closely surround the tube. The tube size, as well as the electrode dimension and spacing may be varied, depending on the fluid viscosity, expected conductivity, frequency of input signal which is to be passed therethrough, dielectric constant of the fluid, and output signal amplitude range desired or expected.

Surrounding, but spaced from the inner cylinders is a shield cylinder 5, of electrically conducting material. The shield cylinder should be long enough that its effect covers the electrostatic end effects of cylinder 2. In FIG. 1A it is shown overlapping completely to the ends of cylinders 3 and 4, although this is not completely necessary. It should overlap at least 25% of the length of cylinder 2 past each end thereof. In the event cylinders 3 and 4 are not connected to ground, during use, it is desirable to have shield 5 overlapping cylinders 3 and 4 by 25% or more.

The conductors of both the electrodes and shields advantageously could be stainless steel, although other conductors could be used depending on the fluid to be measured and the environment expected. Brass has been found to be undesirable in a milk measurement environment, as it appears to react with milk vapors. Compounds of brass have been found to form, providing an apparently dirty environment which is difficult to keep clean.

A lead 6 from cylinders 3 and 4 is brought out, as is a lead 7 from cylinder 2. In the alternative, other ways of connecting cylinders 3 and 4 together may be utilized, for instance through a housing, etc.

It will be seen that an alternating signal will be applied to leads 6 and 7, passing through the capacitor formed by electrode 2 and electrodes 3 and 4, with dielectric formed of tube 1 and the milk passing therethrough. A measurement of the current passed through this capacitor provides an indication of the conductivity of the fluid.

To operate the detection means in a linear region with an accuracy of 1 part in $\alpha$, it has been found that the maximum conductivity measured should be approximately smaller than or equal to $$\frac{LL_A \epsilon f(1.9 \times 10^{-6})}{\alpha d^2 \log (D/d)} \text{ mhos/cm}$$

where
  D is the inside diameter of the conducting cylinders 2, 3, and 4 in centimeters,
  d is the inside diameter of the tube 1 in centimeters,
  L is the distance from the center of conducting cylinder 2 to the closest edge of conducting cylinder 4 or 3 in centimeters,
  $L_A$ is the length of conducting cylinder 2 in centimeters,
  f is the frequency of the applied signal in megahertz,
  $\epsilon$ is the relative dielectric constant of the tube 1.

It has been found that in a practical sensor, for instance having the following dimensions: D = 0.12 inches, d = 0.09 inches, $L_A$ = 1.0 inches, L = 1.0 inches, all converted to centimeters, $\epsilon$ = 3 and f = 10 megahertz, measurements made on the milk therein have been found accurate to one part in $\alpha$ when the maximum conductivity is equal to or smaller than 5 millimhos/cm and $\alpha \simeq 10$.

It will therefore be seen that the conductivity measuring range is heavily dependent on the tube and conducting cylinder diameters, for a given range of fluid conductivity.

Changes in the conductivity of milk from a cow has been found to indicate the presence of mastitis; for instance, in some experimental tests a 15% increase in conductivity in one quarter with respect to the others has shown the presence of that disease. It is therefore desirable to use the sensor of this invention to compute the ratios of conductivities between quarters of a cow, whereupon ratio differences and thus the presence of mastitis will become highly evident.

It has been found that stray currents sometimes flow between the various conducting cylinders and shields, particularly where a group or array of sensor elements are used. The circuit shown in FIG. 2 has been found to reduce leakage currents drawn due to such reasons as interelectrode capacitance. etc.

A radio frequency constant voltage source generator 8 is connected to one of the electrodes, shown for example as center cylinder 2. The other two cylinders 3 and 4 are connected to ground and return to the generator 8. For the example described above, where milk is the fluid of which conductivity is measured, a signal frequency of about 9 megahertz provided by the generator is preferred.

Connected between the conductor leading to cylinder 2 and shield cylinder 5 is an inductor 9, and also connected between the shield cylinder 5 and ground is capacitor 10.

In order to sense the amount of current passing through the milk, the conductor leading to cylinder 2 is passed through the aperture of a toroid 11, although in the alternative the lead connected to cylinders 3 and 4 could have been passed therethrough. This couples the current passing through the milk to inductor 11.

With a 9 megahertz alternating voltage signal applied to the capacitor electrodes 2, 3 and 4 surrounding the tube 1, a current flows through the capacitor, depending on the dielectric constant of the milk. This current, in flowing through the conductor between generator 8 and cylinder 2 induces a current in toroid 11, which is measured by external means. The location of toroid 11 ensures that current in inductor 9 does not pass through toroid 11.

Before flowing milk through the tube 1, or to establish a standard conductivity, capacitor 10 and inductor 9 are varied in capacitance and inductance respectively as in balancing a bridge, to provide a null in the current as sensed from toroid 11. This provides a minimization in the level of leakage current flow which otherwise would degrade the accuracy of the measured readings.

The invention can also be used with multiple sensor elements. For instance, where milk from the four quarters of a cow are to be monitored, four individual sensors would be used, preferably mounted in an array, and located inside the milking machine claw, if one is provided in the milking machine, and which claw is normally located very close to the cow teats.

Again, looking at FIG. 2, additional sensor segments therefore would have their electrodes connected in parallel to the alternating voltage generator 8. In the present example, the central electrode cylinder of each would be connected together and to the lead 7 which interconnects conducting cylinder 2 and generator 8. The specific individual conductors leading to the respective conducting cylinders each should pass through a toroid, shown as toroids 12, 13 and 14. The leads from each of the toroids are then brought out for connection to a detection and current sensing apparatus, which does not form part of this invention.

It should be noted that the individual leads connected to the electrodes in each of the sensors need not be connected directly in parallel with each other to generator 8. It may be desirable to time division multiplex application of the signal to each, and detect the resulting current from the toroids in a similar manner; depending on the specific generation and detection apparatus used, either or both of the application of the signal and the detection thereof may be multiplexed.

FIG. 3 shows in perspective view a series of four sensor elements mounted together for use in the claw of a milking machine. Each is laid on a mounting panel 15 in a parallel and abutting relationship. The shields 5 are soldered together to form a single conducting unit. Each of the dielectric tubes 1, including their cylindrical electrodes, are centrally located within their respective shield cylinders 5. Any well known manner of holding the tubes centrally may be used, such as by annular insulating rings, holes in a covering housing, etc.

Individual leads 7 are brought out from the conducting cylinders covering dielectric tubes 1, through a hole in the shield cylinder 5, to the other side of the mounting panel 15. This provides a convenient structure for leading each of the leads 7 through a toroid, which conveniently can be mounted on the reverse side of mounting panel 15, or on a printed circuit board.

The above-described embodiment has been used, in an example, to measure an aqueous solution of NaCl. Up to 50 parts per thousand, the response has been found to be substantially linear. In one range of the output current curve with conductivity, linearity of better than 1% has been measured.

Figure 4:
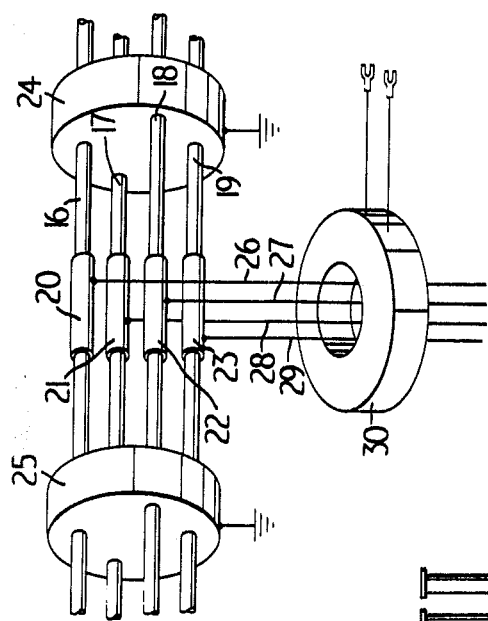

It should be noted that the above-described structure is not the only configuration possible to fabricate this invention. A second embodiment is shown in FIG. 4.

A multiplicity of dielectric tubes 16, 17, 18 and 19 are disposed with conducting cylinders 20, 21, 22 and 23 surrounding each respective tube.

As second electrodes for each of the tubes, end electrodes 24 and 25 are spaced equally separate on each side of the conducting cylinders; they can either take the form of individual cylinders surrounding each respective tube, or can be fabricated of single masses of metal as shown. The end electrodes 24 and 25 connected to ground together. This provides a useful configuration for mounting within a cylindrical housing, the end electrodes forming stops at the ends of the housing. The housing would then be located within the milking machine claw as a sealed unit. The milk from each of the quarters of a cow would be passed through a corresponding tube 16, 17, 18 or 19.

Conductors 26, 27, 28 and 29, conductively connected to a corresponding electrode 20, 21, 22 or 23, are together passed through a toroid 30, the terminals of which are connected to a current detecting and sensing means.

In operation, a source of radio frequency signal is applied to each of the conductors 26, 27, 28 and 29 in turn, as by time division. Current drawn by each of the conductors is controlled by the conductivity of the milk passing through its corresponding tube 16, 17, 18 or 19, whereupon electrodes 24 and 25, with electrodes 20, 21, 22 and 23 form a capacitor with the tubes and milk as dielectric. Accordingly, the current drawn in each of the conductors, picked up in time sequence by toroid 30 provides an indication of the conductivity of the milk in corresponding time sequence.

Figure 5:
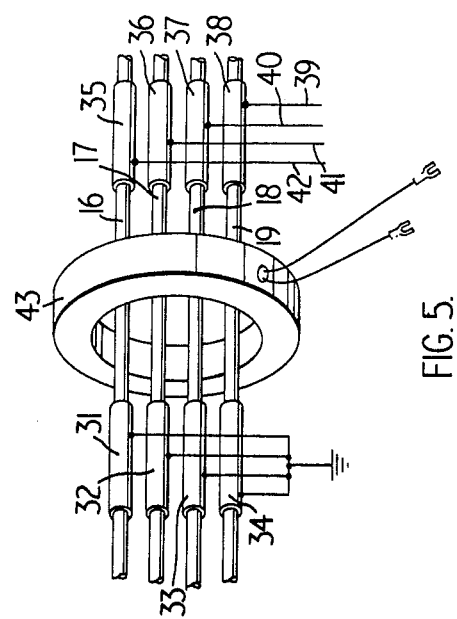
FIGS. 4 and 5 are perspective views of two additional embodiments of the invention.

FIG. 5 shows a third embodiment of the invention. In this case, tubes 16, 17, 18 and 19 carry milk from the respective quarters of a cow. Individual conducting cylinders 31, 32, 33 and 34 provide one electrode for each of the tubes, and are connected together to ground.

Axially spaced from the aforenoted cylinders around the tubes are conducting cylinders 35, 36, 37 and 38 which respectively form other electrodes for the individual capacitors. The cylinders, of course, are held insulated from each other by appropriate means not shown. Each of the cylinders 35, 36, 37 and 38 are adapted to be connected to a time division multiplexed radio frequency signal, via conductors 39, 40, 41 and 42, as described earlier.

Centrally located between the separate groups of conducting cylinders is toroid 43, surrounding all of the tubes 16, 17, 18 and 19 as a group.

In operation, signals are applied sequentially to the capacitors formed by conducting cylinders 35, 36, 37 and 38, and 31, 32, 33 and 34, with dielectric of the respective tubes and the milk flowing through each thereof. Toroid 43 will have a signal induced therein according to the amount of current in the milk within each of the tubes, in time sequence. Accordingly, the output signal from toroid 43, in time sequence, will be representative of the conductivity of the milk from each of the quarters of the cow.

It will be appreciated that the tubes used need not be of circular cross section, nor need the electrodes be cylindrical. The tubes can be rectangular in cross section or of any conduit configuration. The electrodes, in some applications, can simply be a pair of flat plates laterally displaced, applied to the surface of an insulating fluid conduit.

Once having read the present specification, a person skilled in the art will realize that other embodiments may readily be designed within the scope and spirit of the claims. All such alternatives are considered as within the intent and definition of this invention.

The embodiments of the invention in which an exclusive property or privilege is claimed are defined as follows:

1. Apparatus used in determining the conductivity of a fluid, comprising
   a. an insulating tube for passing of fluid therethrough;
   b. current generating means including a radio frequency alternating current source and a pair of laterally spaced conducting plates, each separated by a dielectric from the fluid, for capacitively coupling a radio frequency alternating current signal to the fluid to produce a conductivity current varying with the ionic conductivity of the fluid;
   c. detection means connected to the conductive plates for detecting an alternating current passing through said fluid.

2. Apparatus as defined in claim 1, in which the tube is made of dielectric material, the conducting plates being disposed adjacent the tube.

3. Apparatus as defined in claim 2, in which the conducting plates are each a conducting cylinder surrounding the tube at spaced positions.

4. Apparatus as defined in claim 3, including a third conducting cylinder surrounding the tube, spaced from one of the cylinders a similar distance as the spacing between said pair, and electrically connected to the cylinder opposite the one adjacent said third cylinder.

5. Apparatus for determining the conductivity of a fluid, comprising
   a. a first dielectric tube for passing fluid therethrough;
   b. a first conducting cylinder surrounding and adjacent said tube;
   c. a pair of second conducting cylinders similar to said first cylinder, surrounding and adjacent said tube on different sides of said first cylinder, at equally spaced positions, electrically connected together for applying a radio frequency alternating current signal to the fluid in combination with said first conducting cylinder;
   d. a cylindrical radio frequency shield of diameter greater than said first cylinder, coaxially positioned over, but insulated from, said first and second cylinders; the length of said shield extending at least approximately 25% of the length of said first cylinder on each side thereof.

6. Apparatus as defined in claim 5, further including
   i. a plurality of additional dielectric tubes similar to said first tube,
   ii. a plurality of additional first conducting cylinders, each surrounding and adjacent one of said additional tubes,
   iii. a plurality of additional pairs of second conducting cylinders, each pair surrounding and adjacent a respective one of said additional tubes on different sides of said additional first conducting cylinders, at equally spaced positions, each cylinder of each said pair electrically connected to the other cylinder of its respective said pair,
   iv. a plurality of additional cylindrical shields of diameter greater than said additional first conducting cylinders, each coaxially positioned over, but insulated from, a respective additional first conducting cylinder, the length of each of the shields extending to at least approximately 25% of the length of the respective additional first conducting cylinder on each side thereof,
   v. all of said shields being conductively connected together,
   vi. means for applying said radio frequency alternating current signal respectively between said first and second conductive cylinders and said additional first and second conductive cylinders, and
   vii. individual means for detecting the amplitude of current drawn by individual sets of said cylinders adjacent each tube, the individual amplitudes being indicative of the conductivity of fluid therein.

7. Apparatus as defined in claim 5, further including
   i. a plurality of additional dielectric tubes similar to said first tube,
   ii. a plurality of additional first conducting cylinders, each surrounding and adjacent one of said additional tubes,
   iii. a plurality of additional pairs of second conducting cylinders similar to said additional first conducting cylinders, each pair surrounding and adjacent said one of said additional tubes on different sides of said additional first conducting cylinders, at equally spaced positions,
   iv. a plurality of additional cylindrical shields of diameter greater than said additional first conducting cylinders, each coaxially positioned over, but insulated from, a respective additional first conducting cylinder, the length of each said shields extending to substantially cover the distance between said additional pair of second cylinders,
   v. means for applying said radio frequency alternating voltage signal between said first and second conductive cylinders and said additional first and second conductive cylinders, and
   vi. means for minimizing any differential voltages appearing between said first and second conductive cylinders, as well as additional first and second conductive cylinders.

8. Apparatus as defined in claim 5, including conductor means for applying a radio frequency alternating voltage signal between said first cylinder and said pair of second cylinders, and inductor means disposed in inductive relationship with said conductor means for detecting said alternating current signal.

9. Apparatus as defined in claim 8, in which the inductor means is comprised of a toroid, the conductor means which carries said alternating voltage signal passing directly through the aperture in the toroid.

10. Apparatus as defined in claim 9, in which the conductor means is comprised of fluid flowing in said tube.

11. Apparatus as defined in claim 9 in which said conductor means which carries said alternating voltage signal is a conductor connected to one of either said first cylinder or said second cylinders, further including a second inductor connected between the shield and the conductor outside the shield; the conductor passing through the aperture of the toroid between the point of connection of the second inductor and the first cylinder; capacitor means connected between the shield and the other one of said first or second cylinders outside the shield; the inductance of the second inductor and the capacitance of the second capacitor being variable in the absence of fluid or in the presence of a predetermined fluid conductivity to establish a null in the amount of current conducted via said one of said first or second cylinders.

12. Apparatus as defined in claim 9, further including
   i. a plurality of dielectric tubes similar to said first tube,
   ii. a plurality of additional first conducting cylinders, each surrounding and adjacent one of said additional tubes,
   iii. a plurality of additional pairs of second conducting cylinders, each pair surrounding and adjacent said one of said additional tubes on different sides of said additional first conducting cylinders, at equally spaced positions, each cylinder of each said pair electrically connected to the other cylinder of its respective said pair,
   iv. a plurality of additional cylindrical shields of diameter greater than said additional first conducting cylinders, each coaxially positioned over, but insulated from, a respective additional first conducting cylinder, the length of each of the shields extending to at least approximately 25% of the length of the respective additional first conducting cylinder on each side thereof,
   v. all of said shields being conductively connected together,
   vi. means for applying said radio frequency alternating voltage signal between said additional first conducting cylinders and said additional second conducting cylinders, and
   vii. individual conductors carrying said alternating signal to each set of said cylinders adjacent each tube, each of said individual conductors passing through the aperture of an associated toroid.

13. Apparatus as defined in claim 12, further comprising an alternating voltage generator of radio frequency signal to which all of said individual conductors are connected in parallel, and indicator means connected to said toroids for displaying the amplitude of individual signals induced in each of said toroids.

14. Apparatus as defined in claim 12, in which said signal is approximately 9 megahertz.

15. Apparatus as defined in claim 12, further comprising a milking machine head comprised of a set of teat cups, a mixing bowl, and milk tubes connecting the teat cups to the mixing bowl, each of said tubes being connected as a partial fluid bypass to one of the respective milk tubes.

* * * * *

UNITED STATES PATENT OFFICE
CERTIFICATE OF CORRECTION

Patent No. 4,010,715                    Dated March 8, 1977

Inventor(s) James D. J. Robar et al

It is certified that error appears in the above-identified patent and that said Letters Patent are hereby corrected as shown below:

Assignee incorrect on title page. Should read:

--SED SYSTEMS LTD.--

Signed and Sealed this

Thirtieth Day of May 1978

[SEAL]

Attest:

RUTH C. MASON
Attesting Officer

LUTRELLE F. PARKER
Acting Commissioner of Patents and Trademarks